(12) United States Patent
Pedersen

(10) Patent No.: US 10,362,413 B2
(45) Date of Patent: Jul. 23, 2019

(54) HEARING DEVICE WITH SUPPRESSION OF SOUND IMPULSES

(71) Applicant: GN HEARING A/S, Ballerup (DK)

(72) Inventor: Soren Christian Voigt Pedersen, Valby (DK)

(73) Assignee: GN HEARING A/S, Ballerup (DK)

( * ) Notice: Subject to any disclaimer, the term of this patent is extended or adjusted under 35 U.S.C. 154(b) by 1 day.

(21) Appl. No.: 15/803,545

(22) Filed: Nov. 3, 2017

(65) Prior Publication Data

US 2018/0084350 A1 Mar. 22, 2018

Related U.S. Application Data

(63) Continuation of application No. 15/053,558, filed on Feb. 25, 2016, now Pat. No. 9,930,455.

(30) Foreign Application Priority Data

Dec. 23, 2015 (DK) .................................. 15202409

(51) Int. Cl.
*H04R 29/00* (2006.01)
*H04R 25/00* (2006.01)
*A61F 11/14* (2006.01)

(52) U.S. Cl.
CPC ............ *H04R 25/356* (2013.01); *A61F 11/14* (2013.01); *H04R 25/353* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 7,401,519 B2 * | 7/2008 | Kardous | ................ G01H 3/06 381/56 |
| 2005/0058301 A1 * | 3/2005 | Brown | ............... G10L 21/0208 381/94.2 |

(Continued)

FOREIGN PATENT DOCUMENTS

| | | |
|---|---|---|
| GB | 2 456 297 A | 7/2009 |
| WO | WO 9934642 A1 | 7/1999 |

(Continued)

OTHER PUBLICATIONS

Olsen, Wayne O., "Average Speech Levels and Spectra in Various Speaking/Listening Conditions: A Summary of the Pearson, Bennett, & Fidel (1977) Report", American Journal of Audiology, vol. 7, Oct. 1998, 5 Pages.

(Continued)

*Primary Examiner* — Amir H Etesam
(74) *Attorney, Agent, or Firm* — Vista IP Law Group, LLP

(57) ABSTRACT

A hearing device includes: at least one microphone for converting sound received by the at least one microphone into an audio signal; a sound impulse detector configured for detecting a presence of an impulse in the audio signal; and a signal processor configured for processing the audio signal into a processed audio signal in response to the presence of the impulse in the audio signal as detected by the sound impulse detector; and a receiver coupled to the signal processor for converting the processed audio signal into an output sound signal for emission towards an eardrum of a user; wherein the sound impulse detector is configured for operation in a frequency domain for detecting presence of the impulse in the audio signal.

18 Claims, 11 Drawing Sheets

(52) U.S. Cl.
CPC ......... *H04R 25/505* (2013.01); *H04R 25/652* (2013.01); *H04R 29/001* (2013.01); *A61F 2011/145* (2013.01); *H04R 25/75* (2013.01); *H04R 2225/41* (2013.01)

(56) References Cited

U.S. PATENT DOCUMENTS

| | | |
|---|---|---|
| 2006/0204025 A1 | 9/2006 | Paludan-Mukker et al. |
| 2010/0067722 A1* | 3/2010 | Bisgaard ............. H04R 25/505 381/314 |
| 2013/0010973 A1* | 1/2013 | Ma ...................... H04R 25/356 381/23.1 |
| 2015/0117660 A1* | 4/2015 | Fletcher ............... G10K 11/178 381/72 |

FOREIGN PATENT DOCUMENTS

| | | |
|---|---|---|
| WO | WO 2007025569 A1 | 3/2007 |
| WO | WO 2015135797 * | 3/2015 |

OTHER PUBLICATIONS

Extended European Search Report dated Apr. 5, 2016 for corresponding EP Patent Application No. 15202409.7, 7 Pages.

* cited by examiner

HEARING DEVICE WITH SUPPRESSION OF SOUND IMPULSES

RELATED APPLICATION DATA

This application is a continuation of U.S. patent application Ser. No. 15/053,558, filed on Feb. 25, 2016, pending, which claims priority to, and the benefit of, European Patent Application No. 15202409.7, filed on Dec. 23, 2015, pending. The entire disclosure of the above application is expressly incorporated by reference herein.

FIELD

A new hearing device is provided capable of suppressing sound impulses for ear protection and user comfort.

BACKGROUND

Hearing impaired persons are, compared to persons with normal hearing, more susceptible to discomfort when subjected to sound impulses of high sound pressure levels. Known hearing aids comprise compressors that utilize dynamic sound level compression with time constants that are sufficiently long to avoid distortion of temporal characteristics of speech. The associated recruitment effect combined with a hearing aid increases the discomfort caused by sound impulses with high energy.

SUMMARY

A new hearing device and method are provided that alleviates discomfort caused by sound impulses. Sound impulses are sounds exhibiting high sound pressures during a short time period, such as a time period in the order of milliseconds, such as shorter than 10 milliseconds.

The new method comprises the steps of
converting sound into an audio signal,
subjecting the audio signal to a frequency transformation,
detecting presence of an impulse in the audio signal based on the frequency transformed audio signal, and
processing the audio signal into a processed audio signal in response to detected presence of the impulse in the audio signal,
converting the processed signal into an output sound signal, and
emitting the output sound signal towards an eardrum of a human.

The frequency transformation may be a warped frequency transformation.

The frequency transformation may be a Warped Fourier Transformation, a Warped Discrete Fourier Transformation, a Warped Fast Fourier Transformation, etc.

The warped frequency bands may correspond to the Bark frequency scale of the human ear.

The frequency transformation may be a non-warped frequency transformation.

The frequency transformation may be a Fourier Transformation, such as a Discrete Fourier Transformation, a Fast Fourier Transformation, etc.

The new hearing device comprises
at least one microphone for converting sound received by the at least one microphone into an audio signal,
a sound impulse detector configured for detecting presence of an impulse in the audio signal, and
a signal processor configured for processing the audio signal into a processed audio signal in response to presence of the impulse in the audio signal as detected by the sound impulse detector, and
a receiver connected to an output of the signal processor for converting the processed signal into an output sound signal for emission towards an eardrum of a user, and
wherein
the sound impulse detector is configured for operation in the frequency domain, e.g. utilizing a Fourier Transformation, such as the Discrete Fourier Transformation, the Fast Fourier Transformation, etc., for detecting presence of the impulse in the audio signal.

The sound impulse detector may be configured for utilizing a warped frequency transformation, such as the Warped Fourier Transformation, the Warped Discrete Fourier Transformation, the Warped Fast Fourier Transformation, etc., for transforming the audio signal into a warped frequency domain.

The warped frequency bands may correspond to the Bark frequency scale of the human ear.

The sound impulse detector may be configured for determining a signal level $S_0$ of the audio signal in a frequency band $F_i$ at a time $t_0$ and comparing the determined signal level $S_0$ with a signal level $S_{-1}$ based on at least one previously determined signal level in the frequency band $F_i$ when determining presence of the impulse in the audio signal.

The sound impulse detector may be configured for determining presence of the impulse in the audio signal when the ratio between the signal level $S_0$ of the audio signal in a frequency band $F_i$ determined at time $t_0$ and the signal level $S_{-1}$ based on at least one previously determined signal level in the frequency band $F_i$ is greater than a predetermined threshold $Th_i$ for a predetermined number N of frequency bands $F_i$.

The signal level may be the sound pressure level (SPL) in dB, i.e. the ratio of the root mean square sound pressure and a reference sound pressure of 20 µPa in dB.

Compared to speech, a sound impulse causing discomfort to a human typically exceeds the predetermined threshold in a large number of frequency bands, such as in a number of frequency bands larger than half the total number of frequency bands, for example 10 for a total number of 17 frequency bands, i.e. N may be equal to 10 for a total number of 17 frequency bands.

The threshold may be equal to 10 dB for all frequency bands.

The hearing device may further comprise a sound environment detector for classifying the sound environment into a predetermined set of sound environment classes.

The sound impulse detector may be configured for operation in response to the sound environment class determined by the sound environment detector, for example the threshold $Th_i$ may be a function of the sound environment class determined by the sound environment detector.

A broad-band power level may also be included in the determination of presence of an impulse in order to further distinguish presence of an impulse over the on-set of speech. For example, determination of presence of an impulse may require that the total sound pressure level of the frequency transformed audio signal is larger than a predetermined threshold, such as 75 $dB_{SPL}$, 80 $dB_{SPL}$, etc.

The predetermined threshold value may be adjusted in accordance with user preferences, as explained below in connection with table 1 which is reproduced from W. O. Olsen: "Average speech levels and spectra in various speaking/listening conditions, a summary of the Pearson, Bennett, Fidell (1977) report," American Journal of Audiology, vol. 7, pp. 21-25, 1998.

The hearing device may further comprise a sound impulse suppressor configured for suppressing impulses detected by the sound impulse detector.

The sound impulse suppressor may be configured for attenuating the impulse in one or more frequency bands, such as all of the frequency bands of the hearing device.

The sound impulse suppressor may be configured for attenuating the impulse with an amount that is a function of the sound environment class determined by the sound environment detector.

The sound impulse suppressor may be configured for attenuating the impulse in such a way that the receiver does not emit sound, or substantially does not emit sound, originating from the impulse. For example, if a user wears a hearing aid with the sound impulse detector and the sound impulse suppressor, the sound impulse suppressor may be configured for attenuating the impulse in such a way that the user hears the corresponding sound impulse as if the user did not wear the hearing aid.

Various signal processing parameters, such as detection thresholds, attenuation levels, etc., of the new sound impulse detector and sound impulse suppressor may be adjustable in accordance with user inputs.

The hearing device may be a hearing aid, such as a BTE, RIE, ITE, ITC, or CIC, etc., hearing aid including a binaural hearing aid.

The hearing device may be a headset, headphone, earphone, ear defender, or earmuff, etc., such as an Ear-Hook, In-Ear, On-Ear, Over-the-Ear, Behind-the-Neck, Helmet, or Headguard, etc.

For example, the new hearing device is a new hearing aid comprising a hearing loss processor that is configured to process the audio signal in accordance with a predetermined signal processing algorithm to generate a hearing loss compensated audio signal compensating a hearing loss of a user.

Processing, including signal processing, in the new hearing device may be performed by dedicated hardware or may be performed in a signal processor, or performed in a combination of dedicated hardware and one or more signal processors.

As used herein, the terms "processor", "central processor", "message processor", "signal processor", "controller", "system", etc., are intended to refer to CPU-related entities, either hardware, a combination of hardware and software, software, or software in execution.

For example, a "processor", "signal processor", "controller", "system", etc., may be, but is not limited to being, a process running on a processor, a processor, an object, an executable file, a thread of execution, and/or a program.

By way of illustration, the terms "processor", "central processor", "message processor", "signal processor", "controller", "system", etc., designate both an application running on a processor and a hardware processor. One or more "processors", "central processors", "message processors", "signal processors", "controllers", "systems" and the like, or any combination hereof, may reside within a process and/or thread of execution, and one or more "processors", "central processors", "message processors", "signal processors", "controllers", "systems", etc., or any combination hereof, may be localized in one hardware processor, possibly in combination with other hardware circuitry, and/or distributed between two or more hardware processors, possibly in combination with other hardware circuitry.

A hearing device includes: at least one microphone for converting sound received by the at least one microphone into an audio signal; a sound impulse detector configured for detecting a presence of an impulse in the audio signal; and a signal processor configured for processing the audio signal into a processed audio signal in response to the presence of the impulse in the audio signal as detected by the sound impulse detector; and a receiver coupled to the signal processor for converting the processed audio signal into an output sound signal for emission towards an eardrum of a user; wherein the sound impulse detector is configured for operation in a frequency domain for detecting presence of the impulse in the audio signal.

Optionally, the sound impulse detector is configured for utilizing a non-warped frequency transform for transforming the audio signal into a non-warped frequency domain.

Optionally, the sound impulse detector is configured for utilizing a linear frequency transform for transforming the audio signal into a linear frequency domain.

Optionally, the sound impulse detector is configured for determining a signal level $S_0$ of the audio signal in a frequency band $F_i$ at a time to, and comparing the determined signal level $S_0$ with a signal level $S_{-1}$ based on at least one previously determined signal level in the frequency band $F_i$ when detecting the presence of the impulse in the audio signal.

Optionally, the sound impulse detector is configured for detecting the presence of the impulse in the audio signal when a ratio between the signal level $S_0$ of the audio signal in the frequency band $F_i$ determined at time $t_0$ and the signal level $S_{-1}$ that is based on the at least one previously determined signal level in the frequency band $F_i$ is greater than a predetermined threshold $Th_i$ for a predetermined number N of bands in the frequency Band $F_i$.

Optionally, the sound impulse detector is configured for detecting the presence of the impulse in the audio signal when a ratio between the signal level $S_0$ being a sum of the audio signal in a plurality of frequency bands $F_i$, $F_{i+1}$ determined at times $t_i$, $t_{i+1}$ and the signal level $S_{-1}$ being a sum based on a plurality of previously determined signal level in the frequency bands $F_i$, $F_{i+1}$ is greater than a predetermined threshold $Th_i$ for a predetermined number N of bands in the frequency bands $F_i$, $F_{i+1}$.

Optionally, the sound impulse detector is configured for detecting the presence of the impulse in the audio signal when a broad-band power level of the audio signal is higher than a power threshold level.

Optionally, the hearing device further includes a sound environment detector for classifying a sound environment into a sound environment class, and wherein the sound impulse detector is configured for operation in response to the sound environment class determined by the sound environment detector.

Optionally, the hearing device further includes a sound environment detector for classifying a sound environment into a sound environment class, and wherein the sound impulse detector is configured for operation in response to the sound environment class determined by the sound environment detector; wherein the threshold $Th_i$ is a function of the sound environment class determined by the sound environment detector.

Optionally, a signal processing parameter of the sound impulse detector is adjustable in accordance with a user input.

Optionally, the hearing device further includes a sound impulse suppressor configured for attenuating the impulse in response to the presence of the impulse as detected by the sound impulse detector.

Optionally, the hearing device further includes a sound impulse suppressor configured for attenuating the impulse in response to the presence of the impulse as detected by the sound impulse detector; wherein the sound impulse suppressor is configured for attenuating the impulse with an amount that is a function of the sound environment class determined by the sound environment detector.

Optionally, the sound impulse suppressor is configured for attenuating the impulse in such a way that the receiver does not emit sound originating from the impulse.

Optionally, a signal processing parameter of the sound impulse suppressor is adjustable in accordance with a user input.

Optionally, the hearing device is a hearing aid, and wherein the signal processor comprises a hearing loss processor that is configured to process the audio signal in accordance with a predetermined signal processing algorithm to generate a hearing loss compensated audio signal compensating a hearing loss of the user.

Optionally, the hearing loss processor comprises a dynamic range compressor.

Optionally, the hearing device is a hearing protector comprising a passive dampener configured for dampening sound, and wherein at least a part of the passive dampener is configured for occluding a part of an ear canal of the user.

A method includes: converting sound into an audio signal; subjecting the audio signal to a frequency transformation to obtain a frequency transformed audio signal; detecting a presence of an impulse in the audio signal based on the frequency transformed audio signal; processing the audio signal into a processed audio signal in response to the detected presence of the impulse in the audio signal; converting the processed signal into an output sound signal; and emitting the output sound signal towards an eardrum of a human.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

In the drawings.

DETAILED DESCRIPTION

Various illustrative examples of the new hearing device according to the appended claims will now be described more fully hereinafter with reference to the accompanying drawings, in which various embodiments of new hearing device are illustrated. The new hearing device according to the appended claims may, however, be embodied in different forms and should not be construed as limited to the embodiments set forth herein. In addition, an illustrated embodiment needs not have all the aspects or advantages shown. An aspect or an advantage described in conjunction with a particular embodiment is not necessarily limited to that embodiment and can be practiced in any other examples even if not so illustrated, or if not so explicitly described.

As used herein, the singular forms "a," "an," and "the" refer to one or more than one, unless the context clearly dictates otherwise.

Figure 1:
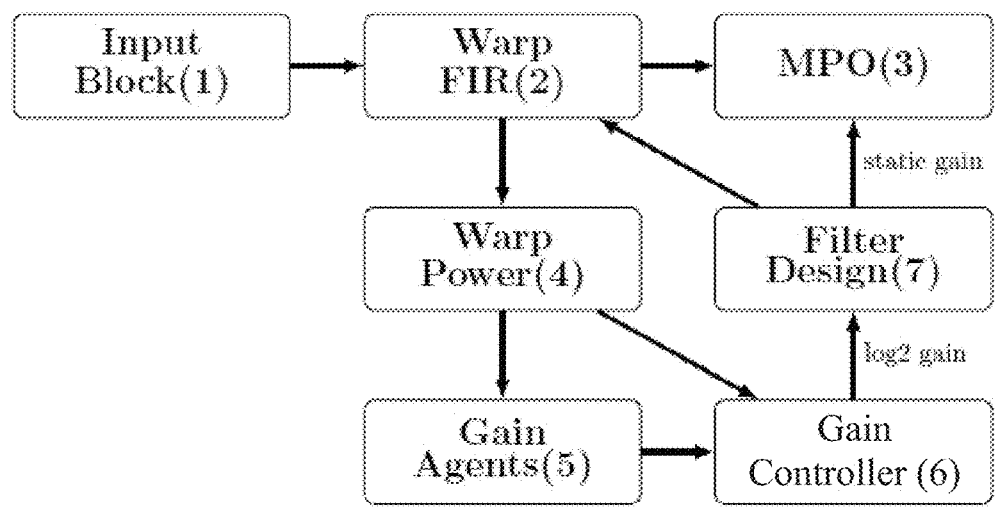
FIG. 1 shows a block diagram of a signal processing scheme of a prior art hearing aid.

FIG. 1 schematically illustrates a prior art hearing aid signal processing scheme 10 with dynamic signal compression performed in a hearing aid compressor well-known in the art of hearing aids.

The known hearing aid compressor performs a warped frequency transformation and controls the gain in 17 warped frequency bands corresponding to the Bark frequency scale of human hearing. The gains are controlled in accordance with the fitting rule of the hearing aid and the hearing loss of the user of the hearing aid so that the dynamic range of a human with normal hearing is compressed into the residual dynamic range of the user with a hearing loss resulting in loss of dynamic range as is well-known in the art of hearing aids. The attack and release time constants are quite long in order to avoid distortion of speech.

The trade-off is that short, intense sounds might be over-amplified and in combination with the rapid increase in perceived loudness, also known as recruitment, this could potentially be a downside of the hearing aid compressor.

Due to the nature of sound impulses, such as door slamming, clinking of silverware, jangling of keys, etc., hearing aid users are often left with discomfort and annoyance in their daily usage.

In many cases a very rare occurring event, influences the hearing device usage in such a way, that the hearing impaired user might lose all the intended benefits from wearing the devices. Turning down the volume or slightly removing the hearing device from the ear, which to some extend is similar to a frequency dependent gain reduction, is something that an algorithm should be able to do both faster and more effective. In order to obtain suitable impulse suppression, impulse detection and response have to be performed with minimum delay, e.g. maintaining un-assisted loudness during the impulse.

For mild hearing losses, protecting against sound impulses could also have another effect; preserving hearing. Persons with normal hearing have what is sometimes referred to as the acoustic reflex which is initiated by high sound pressure levels (SPL). It selectively reduces the intensity of sound transmitted to the inner ear; however with a short delay of approximately 20 ms. Hence, high level impulse sounds such as gun shots may be too short for the muscle to react to, resulting in possibly permanent hearing loss.

Hearing device users with certain combinations of hearing loss and configurations are also disturbed more by less intensive soft sound impulses. This could be the clicking of a computer's keyboard, or rustling paper.

The new sound impulse detector and/or sound impulse suppressor may be adjustable in accordance with user inputs.

In the illustrated embodiment, gain adjustments are performed taking the current gain settings of the hearing aid compressor into account.

The known warped hearing aid compressor signal processing scheme is illustrated in a high level in FIG. 1. The numbering indicates the order of execution within one block of samples. The delay from input to output of the compressor is equal to the time of sampling one block of samples, e.g. a few milliseconds.

Figure 2:
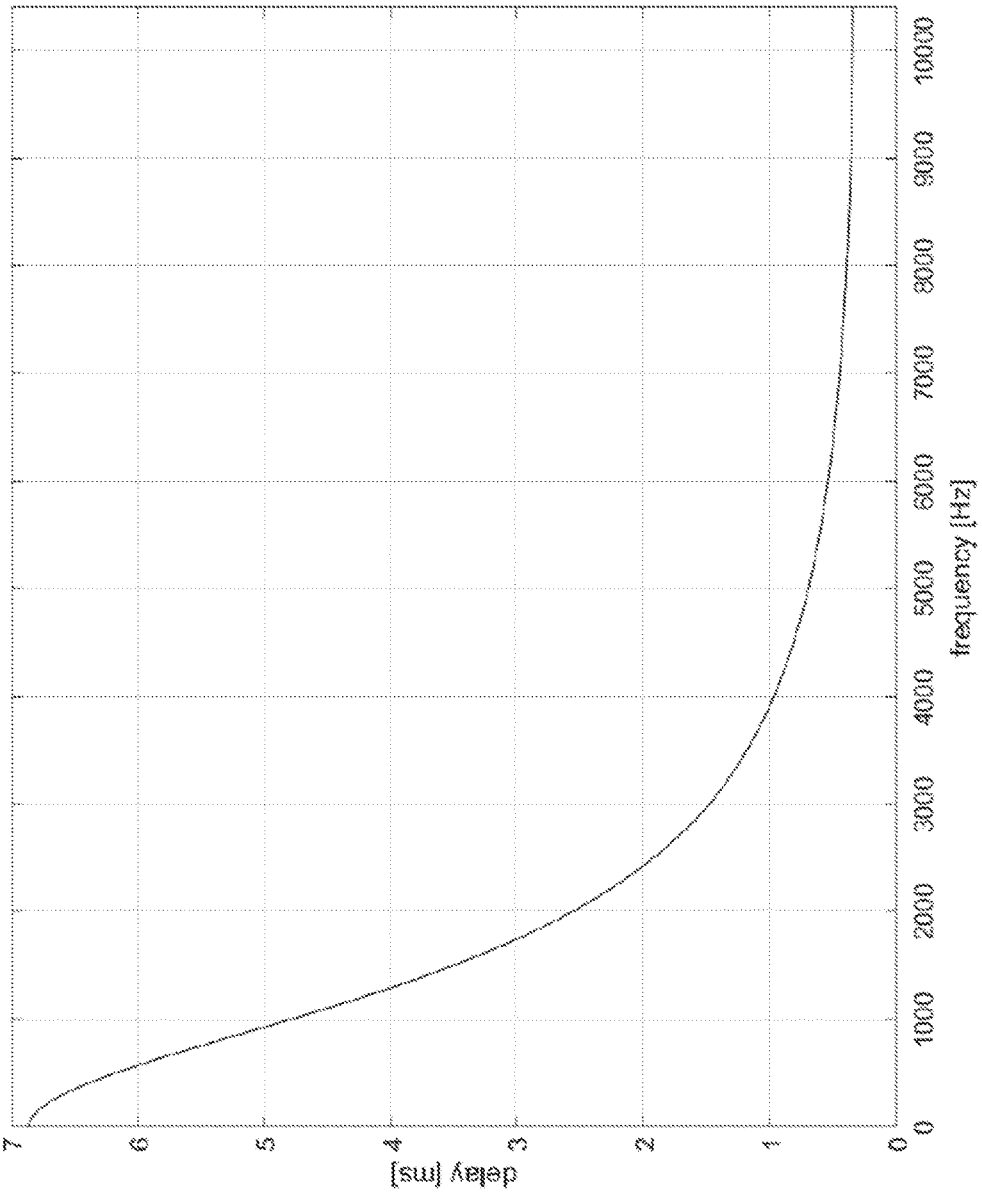
FIG. 2 shows a plot of delay as a function of frequency in a prior art warped delay line.

Estimating power with critical band resolution is achieved by warping the delay line. The all-pass filters serve to implement frequency-dependent unit delays, low frequencies are stretched and high frequencies are compressed. The group-delay as illustrated in FIG. 2, for a high bandwidth configuration, is low at high frequencies while the low frequency area is exposed to a longer group delay. It can be observed that for a compressor system based on the state remaining from the last input sample in each block, the group-delay at high frequencies is much lower than the block rate ~1.5 mS.

In other words, there is a risk that a sound impulse detector based on the warped delay-line potentially underestimates the high frequency part of blocks 2 with an impulse. High bandwidth platforms have a slightly different MPO implementation compared to the normal bandwidth platforms. The MPO has been updated to avoid sudden changes in the static gain operation. A high bandwidth MPO partially applies the static gain changes in intervals of two samples; the full gain change is applied within one block of samples. An impulse gain reduction build on top of the existing MPO, would further imply a change in order to deal with the gain update-delay in the direct sound path.

In order to be able to attenuate impulses, a sound impulse detector is added to the dynamic hearing aid compressor.

Figure 3:
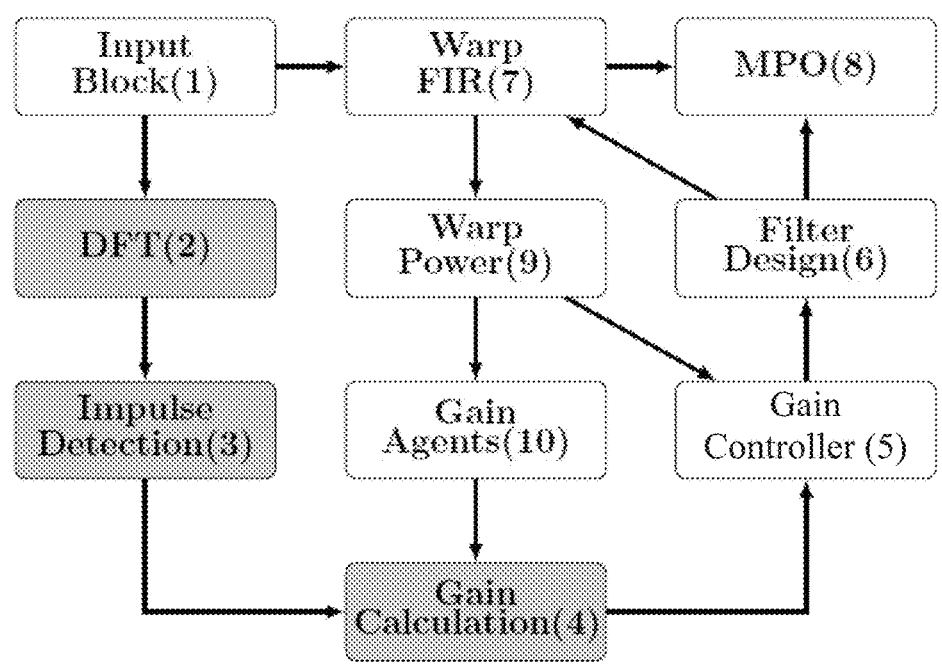
FIG. 3 shows a block diagram of a signal processing scheme according to some embodiments.

The signal processing scheme of a combined sound impulse detector, gain adjustment, and dynamic hearing aid compressor is shown in FIG. 3.

Comparing the execution order of the submodules indicates that the Gain controller and Filter Design are now executed before the direct path processing. The Warp Power is still based on the previous blocks and all gain agents are still processing the same data as before i.e. the dynamic hearing aid compressor is not changed. A new Gain Calculation block has been added before the Gain controller, and an instant change of frequency response can be obtained. If the sound impulse detector and the Gain Calculation block are disabled, the illustrated processing scheme will be identical to the processing scheme shown in FIG. 1, i.e. the processing scheme of the known dynamic hearing aid compressor.

Detecting sound impulses in the frequency domain is performed utilizing a second frequency domain transformation. Addressing complexity, resolution and flexibility, the linear DFT in equation (1) is the starting point for the sound impulse detector.

$$X[n] = \sum_{k=0}^{N-1} x(k)e^{-j\frac{2\pi}{N}nk} \tag{1}$$

Preferably, the sound impulse detector should work on the unprocessed input block. This is illustrated in FIG. 3, where (2) indicates frequency domain transformation, following the new arrived input block of audio samples. Particularly it is of interest how the power rises over time, when looking for impulse patterns. Equation (2) shows the frequency domain power estimate P[n] of the current block.

$$P[n] = abs(X[n])^2 \tag{2}$$

Input blocks of samples, that exhibit impulsive nature must have an approximately instant rise time. In addition, the impulsive characteristic causes a power distribution that spans many bands. A smoothed version of the power estimates per bands ~P [n] is used for the instant rise feature extraction. The parameter α in equation (3) should be chosen sufficiently small, in order to explore the instant rise time of the impulse relative to a short history of background power.

$$\check{P}[n] = P[n](1-\alpha) + \alpha\check{P}[n] \tag{3}$$

For an optimized performance during repetitive impulses, the smoothed power estimates is not allowed to be updated during detected impulses. In addition, the ability to efficiently track the impulse relies on the possibility to compare the frequency domain power of the impulse with the energy just before the impulse onset. Dividing the current power estimate with the smoothed version as in equation (4), can be used as a measure of how much the power in the different bands has raised with the new block of samples.

$$r(n) = \frac{P[n]}{\check{P}[n]} \tag{4}$$

For implementation complexity reasons, the rise measure r (n), could advantageously be implemented in the $\log_2$ domain. The precision of the $\log_2$ is found to be accurate enough, and the remaining part of the sound impulse detector could improve by having decision and threshold implemented in the logarithmic domain, equation (5).

$$r(n) = \log_2(P[n]) - \log_2(\check{P}[n]) \tag{5}$$

It could be argued that, due to the window size, the power estimates are poor for the lowest bands. For simplicity and in order to align with the existing hearing device platform the number of bands L is defined as equation (6)

$$L = \frac{N}{2} + 1 \tag{6}$$

where N is the size of the DFT and accordingly, in a non-overlap implementation, is equal to the processing block-size. Now, a vector $r_t$ build of L bands rise measures in the $\log_2$ domain can be constructed $$r_t[r(0), r(1), \ldots, r(L-1)] \tag{7}$$

wherein t is block rate which for a high bandwidth hearing device platform is $$T_{block} = N \cdot \frac{1}{fs} \approx 1.5 \text{ ms} \tag{8}$$

In effect the block rate in eq. (8) also sets the lower limit of the impulse rise time that the sound impulse detector can observe. Keeping in mind that this limit is not to be confused with the scheme in FIG. 3, which can apply gain reduction instantly with no delay from the detection point. One major point of concern for a sound impulse detector will always be whether it distinguishes between impulse sounds like door slamming, cutlery etc. and speech onset, which is the portion of vocalization where impulse-like characteristics can be ascertained. One way of addressing this issue could be to include a threshold that would operate on the vector $r_t$. Now eq. (9) defines a measure of how many bands in the present power estimate exceeds this threshold.

$$R_t = \text{sum}(r_t > \text{RiseThreshold}) \tag{9}$$

The threshold in eq. (9) would be defined in the $\log_2$ domain. Compared to speech, impulse noises that are annoying in nature, for hearing device users, tends to span power over most of the frequency power bands. Defining that the sum of power bands with instant rise time $R_t$ should be above 10, adds another dimension to the task of addressing speech vs. impulse noise in the sound impulse detector. At this point a true/false parameter of impulse detection is available.

A final broadband power threshold is also applied to ensure that only impulsive blocks above a particular sound-pressure level are detected. This threshold is applied in order to configure the sensitivity of the sound impulse detector. For end-users that only find intense impulses like door slams annoying, this threshold can be increased compared to users who are disturbed by more weak impulses, defined like the clicking of a computer keyboard, clattering dishes etc. For example firecrackers can reach level as high as 180 $dB_{SPL}$.

Table 1 below shows the speech levels (non-weighted SPL) of casual, normal, raised, loud, and shouted speech by males, females, and children:

TABLE 1

|  | Casual | Normal | Raised | Loud | Shouted |
|---|---|---|---|---|---|
| Females | 54 | 58 | 65 | 72 | 82 |
| Males | 56 | 61 | 68 | 77 | 89 |
| Children | 56 | 61 | 67 | 75 | 82 |

A broadband power threshold of the sound impulse detector has a naturally lower limit as indicated in table 1 which is reproduced from W. O. Olsen: "Average speech levels and spectra in various speaking/listening conditions, a summary of the pearson, bennett, fidell (1977) report," American Journal of Audiology, vol. 7, pp. 21-25, 1998.

In order to apply even more robustness towards knowing the difference between speech onset and targeted impulse sounds, this threshold must be set high enough to operate on top of the normal speech production area. The pseudo code in Algorithm 1 summarizes impulse detection of the sound impulse detector. The output parameter of the detection algorithm is detect, which holds values between zero and one ($0 \leq \text{detect} \leq 1$). For detect to reach zero after an impulse has decayed to a state where it is no longer exploring impulsive characteristics, or does not longer comply with the broadband power threshold, a logarithmic release time is applied. The parameter $\alpha_{detect}$ is used to specify the release time, while the attack time of detect is instant.

Figure 4:
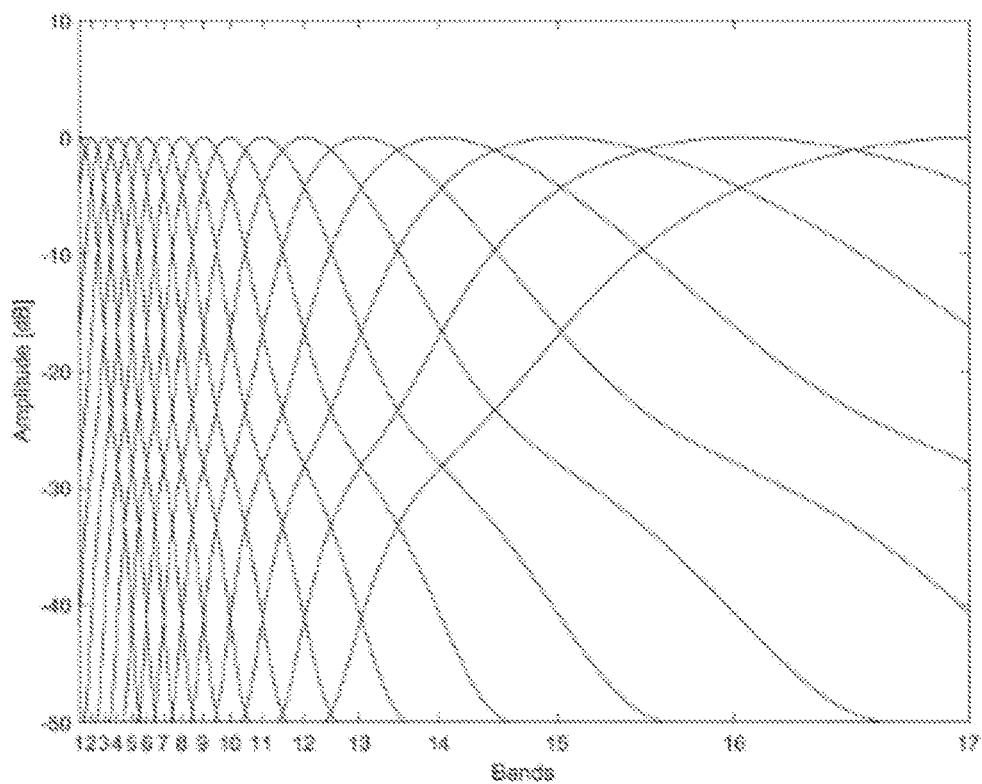
FIG. 4 shows a plot of warped frequency bands.
Figure 5:
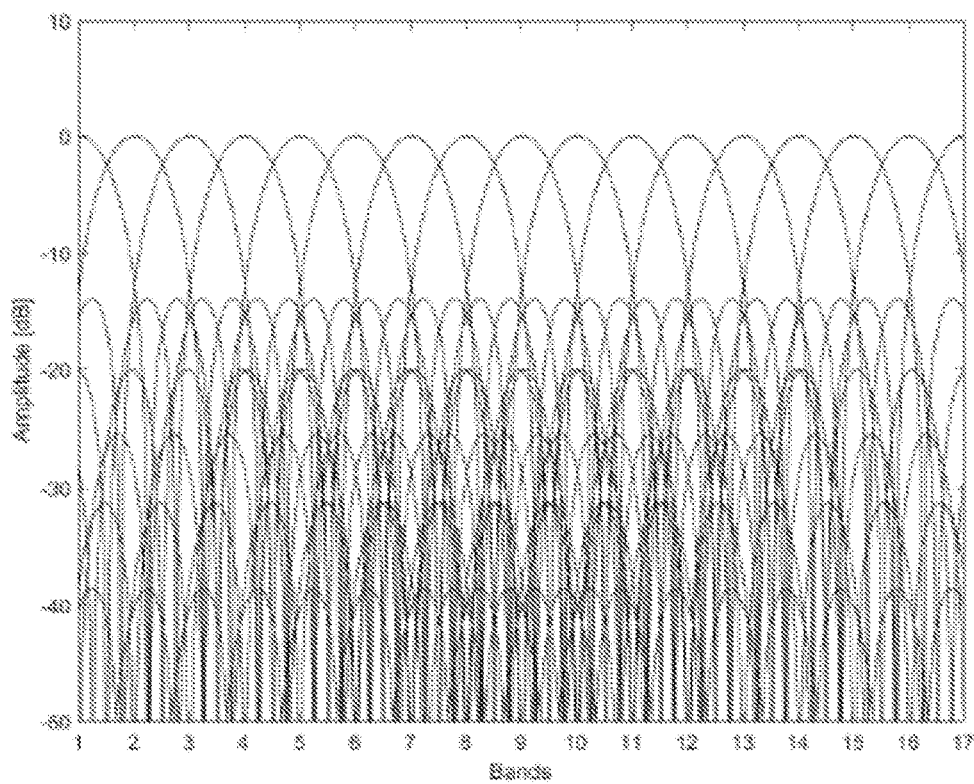
FIG. 5 shows a plot of frequency bands of an sound impulse detector according to some embodiments.

A frequency-warped FIR filter can be designed by replacing the unit delays in the conventional FIR filter with all-pass filter sections. It serves to match the frequency resolution of the compression system to the resolution of the human auditory system. Additionally the warped filter has a higher group-delay at low frequencies than a conventional filter for the same low frequency resolution. As discussed earlier, the short delay at high frequencies is problematic for a sound impulse detector e.g. under-sampling can lead to false detection. In addition, the frequency resolution of a DFT based on a warped delay line can limit the performance of the detection scheme as well. The warp Compressor system, or more important the power estimator, is based on the warped delay line utilizing the all-pass transfer function in equation 10.

$$H(z) = \frac{a + z^{-1}}{1 + az^{-1}} \tag{10}$$

where a is the warping parameter. Combined with the warp window this leads to the 17 bands illustrated in FIG. 4. The warped frequency scale gives a much better match to auditory perception compared to a linear based system. However, serving to detect and differentiate impulse noises from the daily sound environment including own and surrounding speech, the warp-based DFT delivers poor performance. In order to use the number of frequency bins with instant power rise as a feature for detecting impulsive input blocks, a much better resolution is needed in the highest bins. In addition the warp window is constructed to smear adjacent bins to avoid drastic gain differences by the filter designer. The sound impulse detector utilizes a 32-point linear FFT with a Tukey window. FIG. 5 illustrates the frequency resolution of the 17 bands. This configuration will not favour speech-like signals. Another choice could be to use a warped delay line with a positive warping factor. This would further increase the resolution of the highest bins, leading to a detection even more focused on instant power increase in regions not dominated by speech. The primary disadvantage of a detection scheme based on a parallel warped delay line is the computational cost of replacing unit delays with first-order all-pass filters.

3.2 Spectral Leakage

The DFT implicit assumes that the signal is periodic in the time frame. When the input block is not periodic then leakage occurs. Leakage results in misleading information about the spectral amplitude and frequency. For the sound impulse detector, the worse impact is leakage to adjacent bins, which might lead to false detection. The sound impulse detector relies on identification of bands with rapid increase of sound power; spectral leakage contributes to the risk of false detection. A DFT window can be applied to reduce the effects of leakage.

$$\hat{x}(n) = x(n)w(n) \tag{11}$$

$$\hat{x}_t[\hat{x}(0), \hat{x}(1), \ldots, \hat{x}(N-1)] \tag{12}$$

$$X_t = DFT(\hat{x}_t) \tag{13}$$

The Gain calculation block may reduce broad-band gain, e.g. the gain in all of the frequency bands, in a plurality of the frequency bands, such as in more than half of the frequency bands, of the compressor in order to attenuate the impulse.

The Gain calculation block may restore natural loudness of signals like slamming doors, clinking of silverware or jangling of keys, in response to impulse detection. These are all examples of sounds that are part of the daily sound environment, but in most cases will generate an unnatural and painful representation at the ear-drum of the hearing device user. Focusing on the end-user and what causes the discomfort, the Gain Calculation block must be able to address the over-amplification of short duration impulsive signals. Most likely the un-natural reproduced segments is causes by the linear part of the prescribed gain i.e. the $G_{50}$ gain is applied for high energy impulse signals. In other words, what causes the discomfort is end-user dependent and most likely described by the $G_{50}$ gains. This also means that the sound impulse suppressor needs to control gain independently in the 17 frequency bands, in order to match the behaviour of the warp system.

The sound impulse suppressor is configured for attenuating the impulse to a comfort level still being descriptive of the acoustic environment. A very simple approach that does not add significant complexity to the run-time part of the algorithm could be to utilize a gain look-up table. A look-up table would map the broadband power of an impulse section, to a reduction vector, with the needed gains for the 17 warped bands. A given fitting rule is used to reach the prescribed gain based on the hearing threshold. In a two power bands configuration, the prescribed gain is implemented by the target $G_{50}$ and $G_{80}$ gains. Define a broadband power threshold vector B as a starting point $$B=[b(0),b(1),\ldots,b(P-1)] \quad (14)$$

where P is the power table size i.e. the resolution of the steps that can be achieved. The span of power, or the SPL area that sound impulse suppressor should work within is defined as $$\text{power\_span}=B[P-1]-B[0] \quad (15)$$

The target gains are now mapped linearly into this area by means of the parameters min reduction and max reduction. Where min reduction in dB defines the reduction at the lower boundary of the B vector and max reduction defines the reduction at the top of the vector. E.g. it is defined how much of the target gains, $G_{50}$, that the sound impulse suppressor will correct for at a given SPL. Use the relative distribution of broadband power level thresholds ΔB in order to normalize this vector $$\hat{B} = \left[0\, cumsum\left(\frac{\Delta B}{\text{power\_span}}\right)\right] \quad (16)$$

Figure 6:
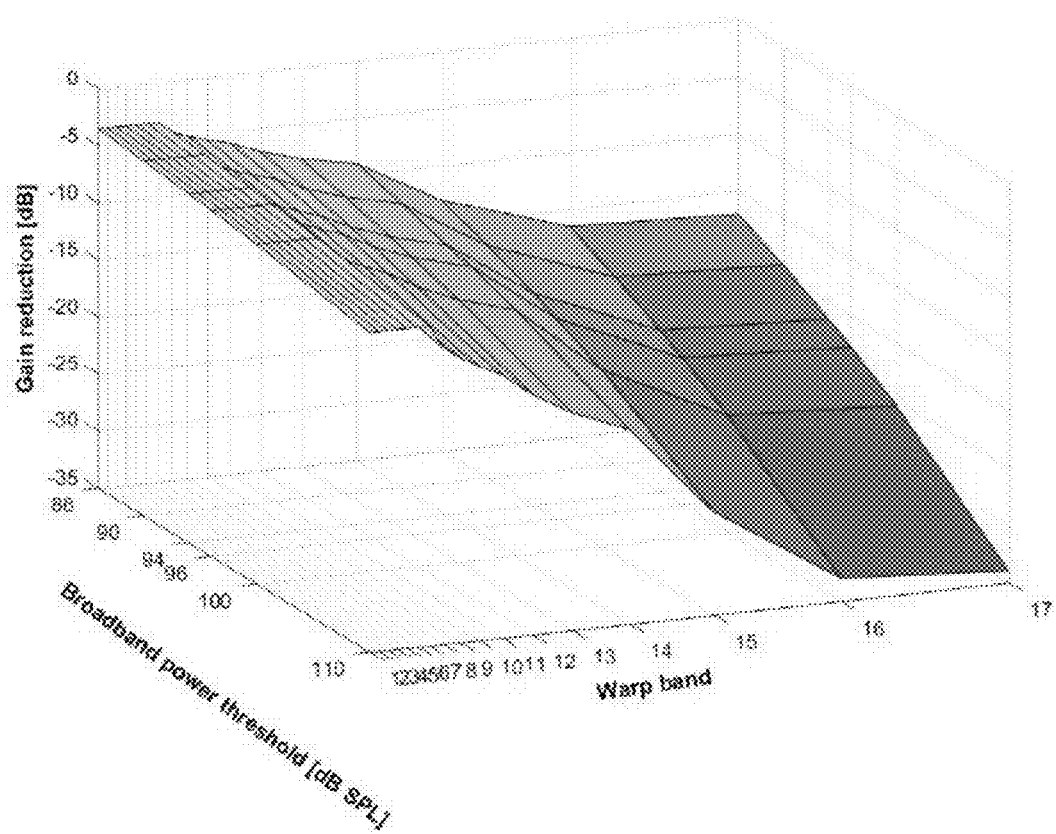
FIG. 6 shows a plot of gain reduction as a function of broadband power according to some embodiments.

The normalized vector $\hat{B}$ can be used to linearly interpolate from the two-dimensional space defined by min reduction and max reduction, into the dimension of the B vector. The outcome is a vector with gain reduction ratios, in dB, per broadband power level. These reduction numbers are relative to the $G_{50}$ target gains and the final the sound impulse suppressor gains are now defined as a P by 17 matrix G. If min reduction is set to 6 dB, the sound impulse suppressor will apply half of the target gain in reduction during an impulse with the lowest broadband power. This will then linearly increase up to e.g. max reduction set to 0 dB, where the sound impulse suppressor will reduce the gains equal to the target gains i.e. fully compensate for the AGCI (Automatic Gain Control-Input) gains. FIG. 6 illustrates how the target $G_{50}$ gains are mapped to the sound impulse suppressor gain reductions. This example has the broadband power threshold vector B set to $$B=[86\ 90\ 94\ 96\ 100\ 100][dBSPL] \quad (17)$$

and the target $G_{50}$ gains used was $$G_{50}=[7\ 7\ 7\ 7\ 7\ 7\ 9\ 10\ 11\ 12\ 14\ 16\ 18\ 26\ 33\ 34] \\ [dB] \quad (18)$$

With min reduction set to 6 dB and max reduction set to 0 dB, it is observed how the gain reduction gradually increases from half the $G_{50}$ target gains, at an impulse broadband power of 86 dB SPL, up to full compensation at 110 dB SPL. When maximum broadband power is reached in the B vector, the sound impulse suppressor gain reduction is locked to this level. In addition, the broadband power threshold used in the detection part should be the same value as the first entry of the B vector. This will align the sound impulse detector and the gain calculation block with respect to active area of operation.

In the attempt of securing listening comfort for a broad representation of hearing threshold fittings, the ability of adjusting the sensitivity of the sound impulse detector is needed. Users might express special needs and annoyance levels e.g. some hearing impaired might feel discomfort even for less intensive impulse-like sounds like clicking of a computers keyboard, rustling paper etc. There might also be a need for different sensitivity in order to address acclimatization for first-time hearing device users. A simple mild, medium and strong approach is preferred. This can be achieved by addressing the broadband power levels during impulses different, i.e. by defining the vector B per mode. An example of how the sound impulse detector modes could be configured is shown in table 2 listing sound impulse detector modes (mild, medium, strong) aligned with broadband power thresholds dB SPL.

TABLE 2

| | low | . | . | . | . | high |
|---|---|---|---|---|---|---|
| Mild | 90 | 94 | 98 | 100 | 104 | 114 |
| Medium | 86 | 90 | 94 | 96 | 100 | 110 |
| Strong | 75 | 78 | 80 | 84 | 86 | 90 |

In combination with the B vector being set per mode, max reduction and min reduction could also be included. This enables the sound impulse detector and sound impulse suppressor to define modes by means of the levels of where to reduce gains, and indeed also how much to reduce gain.

Figure 7:
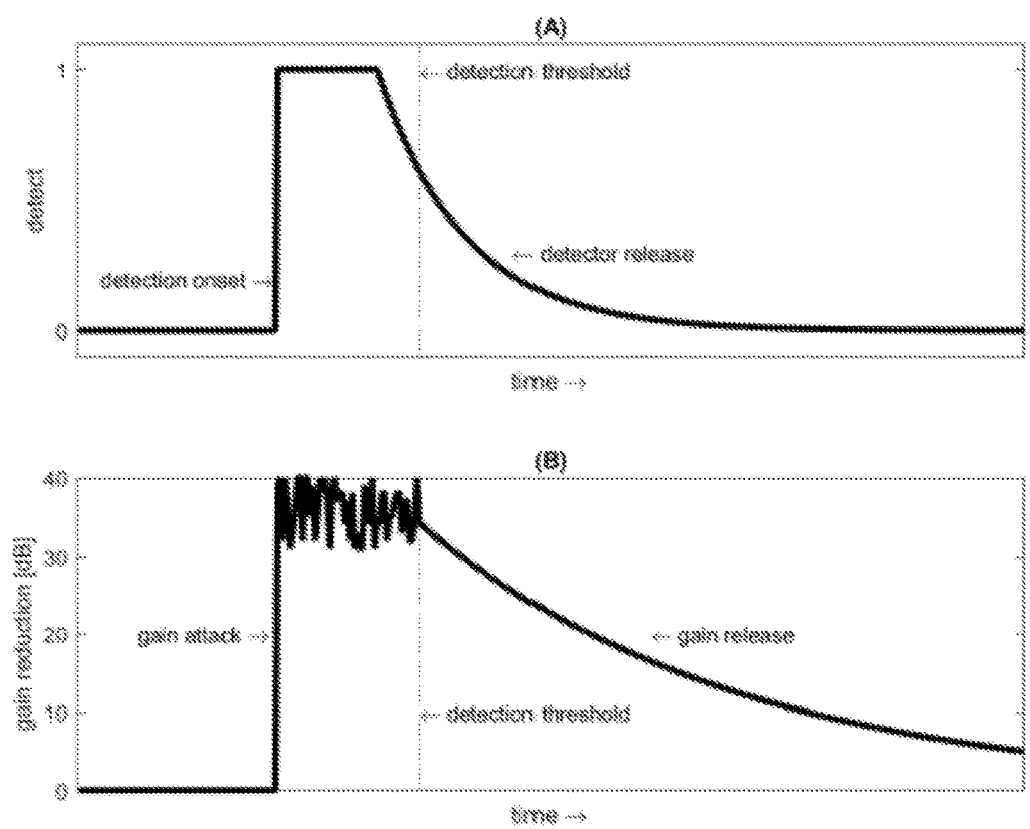
FIG. 7 shows plots of impulse detection and gain reduction as a function of time according to some embodiments.

When dealing with discomfort, by reducing gain during impulse sounds, the sound impulse suppressor applies the smallest attack time achievable. This is possible as already observed in the re-arranged warp system in FIG. 3. The broadband power is expected to vary during an impulse; the impact could be that the gain reduction applied will fluctuate causing distortion. This potential issue increases with more extreme settings of the modes in table 2, e.g. if a mode spans a large area of sound pressure levels. A way of addressing fluctuating sound impulse suppressor gains could be to apply an impulse onset detection parameter. In FIG. 7 (A) this is illustrated. An impulse onset detect is defined as being the point in time where the previous block was not detected as part of an impulse sequence, and an impulse is detected in the present block.

This is Described as $$\text{onset} = \begin{cases} \text{true,} & \text{if(predetect == 0 \&\& detect == 1)} \\ \text{false,} & \text{otherwise} \end{cases} \quad (19)$$

Now, the algorithm can distinguish between impulse onset and the part of the impulse where all other conditions are still valid i.e. in the middle part of the impulse. The strategy for how to apply gain reduction is to use symmetric smoothing of the gain in blocks preceding the block where impulse onset is detected. The onset block will determine the gain starting point according to the current broadband power.

Short impulse-like signals are in some situations part of the spatial awareness experienced by the hearing impaired. In the sense that room reverberation is providing perceptual awareness about the characteristics and size of the room. Optimally, the gain reduction release time must be set according to the acoustic environment e.g. with respect to the reverberation time of the room, hall etc. The release time, in combination with the normal AGCI attack time, should be set so that the early reflections are still suppressed, while late reflections are perceived with normal loudness. For speech intelligibility, early reflections are very important for both normal hearing and hearing impaired persons, while the late reflections often degrades the ability to understand speech in noise. For impulse signals this is opposite, in the sense that late reflections adds to the perception of the room characteristics. For a hearing device user, early reflections, which could still include high energy at some frequencies, would still be over-amplified and though add to the discomfort (given that the AGCI release time is long compared to the arrival of the early reflections).

The sound impulse suppressor may have a broadband gain release time, i.e. all bands are configured to the same time constants and this parameter is not adapted in any way during run-time. During the release time the gain reduction provided by the sound impulse suppressor will decade. This serves to smooth the transition between the sound impulse suppressor actively reducing the impact of the impulse, and restoring normal AGCI control of input related gain handling. The release of gain reduction will be based on a threshold on the detect parameter, FIG. 7 (A). This parameter can be used in the decision of when the impulse has decreased its strength to a point where it can be defined as completed. At this point the gain release takes over, FIGS. 7 (A) and (B) illustrates the usage of a detection threshold.

Figure 8:
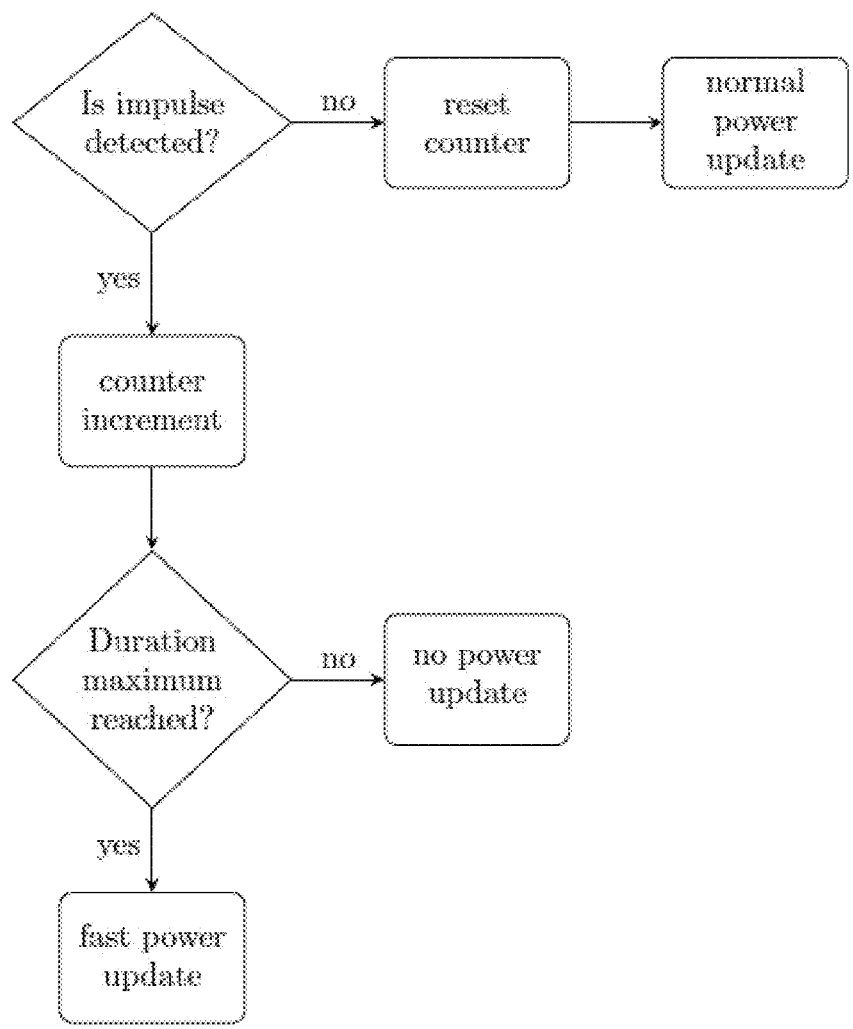
FIG. 8 shows a flow-chart of power estimation calculation according to some embodiments.
Figure 9:
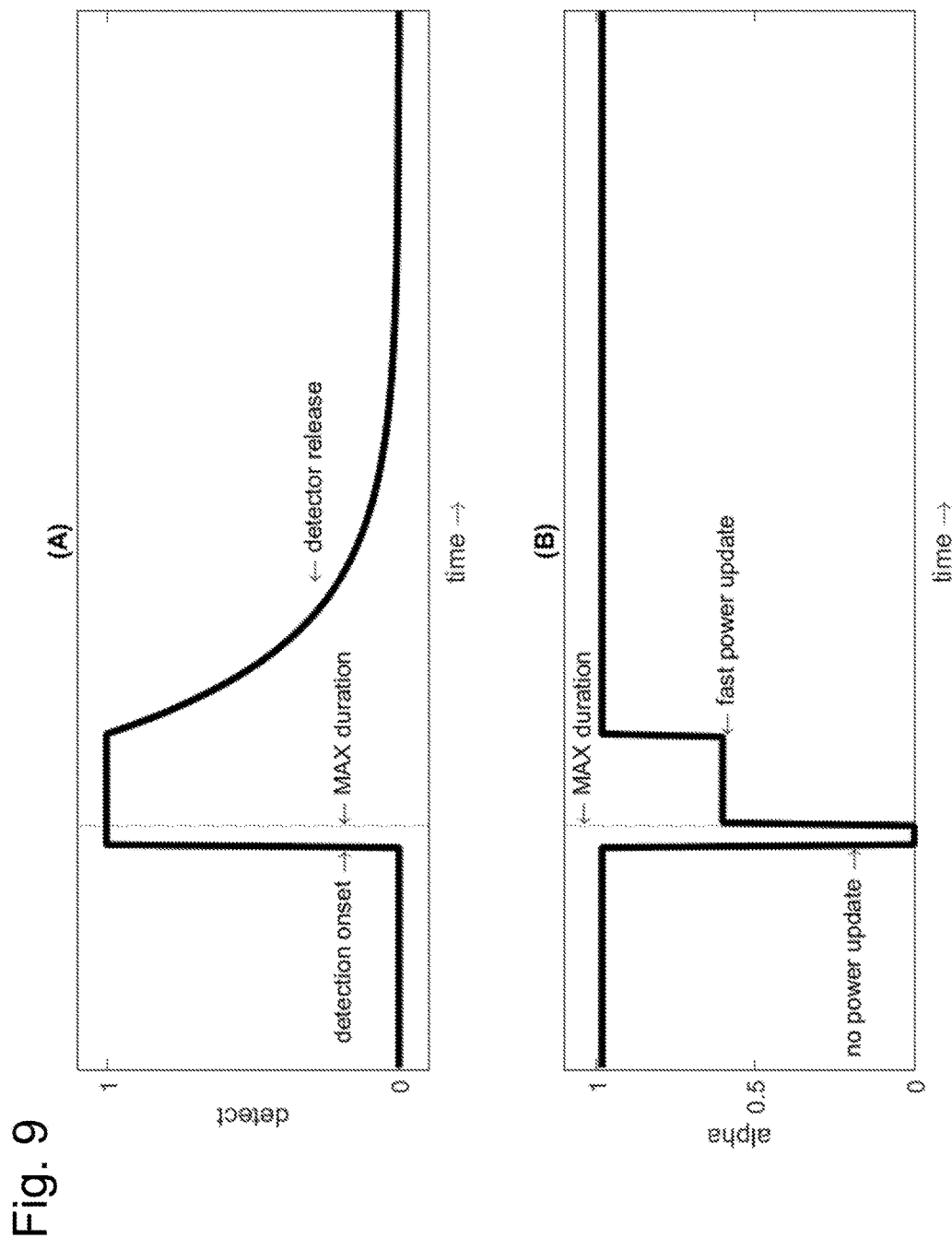
FIG. 9 shows plots of impulse detection and α-values as a function of time according to some embodiments.
Figure 10:
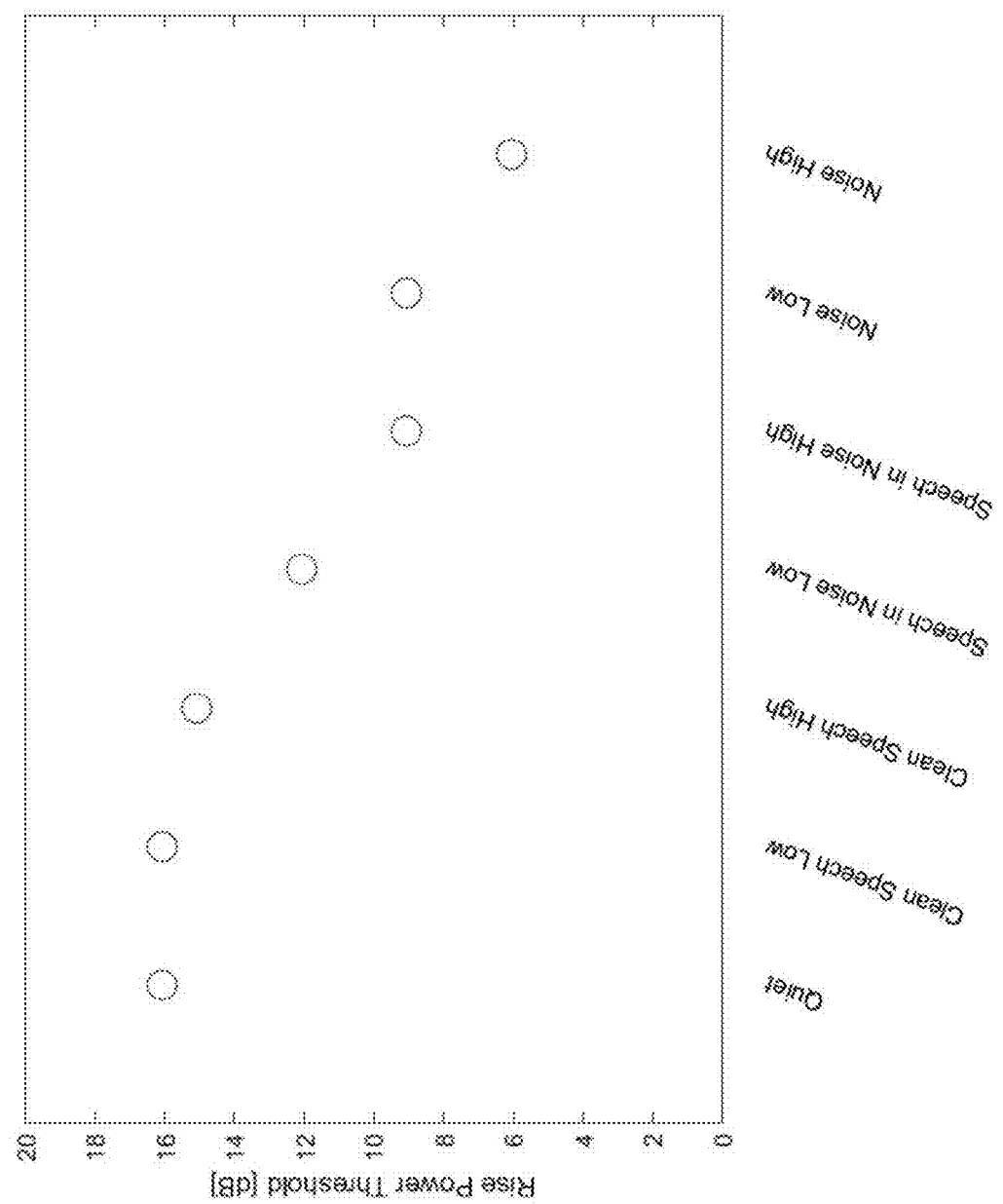
FIG. 10 shows a plot of rise power thresholds for different sound environments according to some embodiments.

A way of detecting and reacting upon impulsive inputs has been described in the previous sections. It is clear that input signals with impulsive onset and a certain length will have the ability to lock the detecting state of the algorithm. A measure of the duration of an impulse and a maximum impulse duration definition is needed. In order to hand-over signals that in nature exploits impulse start conditions, but are much longer in duration, the sound impulse suppressor is configured to fade out and leave the gain handling to the normal warp compressor system. If a signal has impulsive onset followed by a long sequence with energy in many bands, the power estimation will, by design, be locked by the sound impulse detector. The consequence is that these types of sounds will be attenuated by the Gain Calculation block for much longer time that required, i.e. it will overlap with the normal warp compressor system which over time will reduce gains. E.g. the start of a lawnmower will typically go from a very quiet condition, over a short impulsive part and then stay noisy in many bands for a longer period. A definition of the maximum duration of the impulses the sound impulse suppressor should handle, and how to measure and fade-out is needed. A very elegant way of controlling the sound impulse detector part in relation to the duration of the impulse is to adaptively control the parameter in equation (3). Based on the information of where the current detection estimate is in time, it is possible to control the update rate of the frequency band power estimate smoothing. The flow-chart in FIG. 8 illustrates how to control and update the power estimator part of the detector. Based on a defined maximum duration count it is possible to decide the smoothing rate based on the parameter $\alpha$. An $\alpha$-value going towards zero will simply stop the smoothing of the frequency bands power estimates. This is the preferred setting in the sequence following the onset of an impulse, i.e. stop updating. For normal operation, where no impulse is detected a rather high value of $\alpha$ is needed in order to base the detection decision on the history of energy per bands. A fast power update is needed when the maximum duration of an impulse is reached. The consequence of lowering the $\alpha$-parameter, a fast update speed, will be that the power estimates will quickly adapt to the levels which is currently experienced by e.g. a lawnmower. The difference between the current estimate and the smoothed estimates will no longer exploit instant rise and the detection scheme will resign to release mode, and we can apply normal $\alpha$ values for a rather slow update rate again. The sequence of changing the $\alpha$-parameter based on the detection value is shown in FIG. 9.

At this point the differentiation in attenuation applied by the sound impulse suppressor is based purely on the broadband power. Gain vectors based on the prescribed gain are calculated on-line and applied according to the estimated broadband power. This scheme seems to favour the situations close to the $G_{50}$ knee-point, is could be an advantage to include another knee-point to reach a stage where the applied gain is steered towards the present sound pressure level. One solution could be to utilize the classifier classes which to some extend includes information about the sound pressure level of the environments. Table 3 lists the sound pressure levels related to each of the classifier output classes. According to the table, it makes sense to add another gain table and base the calculated gain tables on a knee-point at approximately 75 $dB_{SPL}$. The classifier environments can now be used to steer the gain reduction tables in order to achieve that the sound impulse suppressor takes into account the current estimated sound environments. E.g. silent environments, where the prescribed gain are in the linear area, maps to higher gain reductions and high noise environments, where the gain operates in the compression area, should attend less gain reduction from the sound impulse suppressor.

Figure 11:
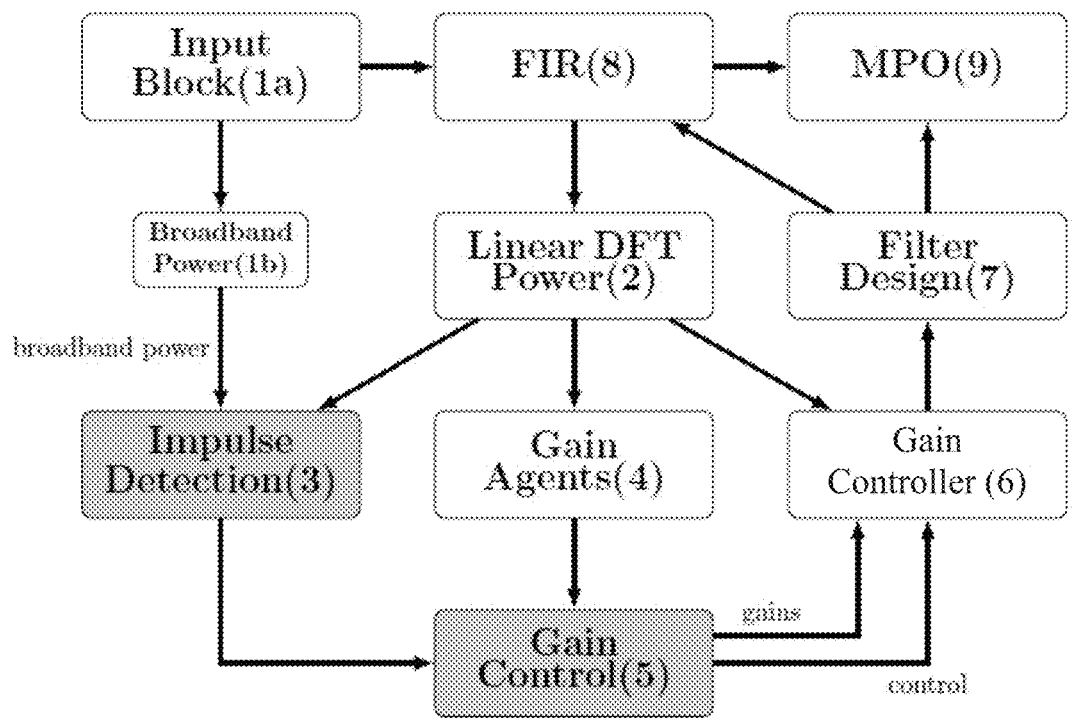
FIG. 11 shows a block diagram of a signal processing scheme according to some embodiments.

According to another embodiment with a signal processing scheme shown in FIG. 11, e.g. for a hearing protection device, wherein the warped delay line and warped power estimates are not present, a more simple sound impulse detector and sound impulse suppressor can be utilized. In addition applications where the gain reduction is not to be associated with a hearing loss or prescribed gain, the impulse detection block of the sound impulse detector could provide input to a gain control unit rather than a gain calculation unit of the sound impulse suppressor. A gain control unit could control several parameters of the Gain controller given inputs from other gain agents and the Impulse Detection block.

Although particular embodiments have been shown and described, it will be understood that they are not intended to limit the claimed inventions, and it will be obvious to those skilled in the art that various changes and modifications may be made without departing from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. A hearing device comprising:
    at least one microphone for converting sound received by the at least one microphone into an audio signal;
    a sound impulse detector configured for detecting a presence of an impulse in the audio signal; and
    a signal processor configured for processing the audio signal into a processed audio signal in response to the presence of the impulse in the audio signal as detected by the sound impulse detector; and
    a receiver coupled to the signal processor for converting the processed audio signal into an output sound signal for emission towards an eardrum of a user;
    wherein the sound impulse detector is configured for operation in a frequency domain for detecting presence of the impulse in the audio signal.

2. The hearing device according to claim 1, wherein the sound impulse detector is configured for utilizing a non-warped frequency transform for transforming the audio signal into a non-warped frequency domain.

3. The hearing device according to claim 2, wherein the sound impulse detector is configured for utilizing a linear frequency transform for transforming the audio signal into a linear frequency domain.

4. The hearing device according to claim 1, wherein the sound impulse detector is configured for determining a signal level $S_0$ of the audio signal in a frequency band $F_i$ at a time $t_0$, and comparing the determined signal level $S_0$ with a signal level $S_{-1}$ based on at least one previously determined signal level in the frequency band $F_i$ when detecting the presence of the impulse in the audio signal.

5. The hearing device according to claim 1, wherein the sound impulse detector is configured for detecting the presence of the impulse in the audio signal when a ratio between (1) a signal level $S_0$ of the audio signal in the frequency band $F_i$ determined at time $t_0$ and (2) a signal level $S_{-1}$ that is based on at least one previously determined signal level in the frequency band $F_i$ is greater than a predetermined threshold $Th_i$.

6. The hearing device according to claim 1, wherein the sound impulse detector is configured for detecting the presence of the impulse in the audio signal when a ratio between (1) a a first value $S_0$ being a sum of signal levels of the audio signal in a plurality of frequency bands $F_i$, $F_{i+1}$ determined at times $t_i$, $t_{i+1}$ and (2) a second value $S_{-1}$ being a sum based on a plurality of previously determined signal levels in the frequency bands $F_i$, $F_{i+1}$ is greater than a predetermined threshold $Th_i$.

7. The hearing device according to claim 1, wherein the sound impulse detector is configured for detecting the presence of the impulse in the audio signal when a broad-band power level of the audio signal is higher than a power threshold level.

8. The hearing device according to claim 1, further comprising a sound environment detector for classifying a sound environment into a sound environment class, and wherein the sound impulse detector is configured for operation in response to the sound environment class determined by the sound environment detector.

9. The hearing device according to claim 5 or 6, further comprising a sound environment detector for classifying a sound environment into a sound environment class, and wherein the sound impulse detector is configured for operation in response to the sound environment class determined by the sound environment detector;
    wherein the threshold $Th_i$ is a function of the sound environment class determined by the sound environment detector.

10. The hearing device according to claim 1, wherein a signal processing parameter of the sound impulse detector is adjustable in accordance with a user input.

11. The hearing device according to claim 1, further comprising a sound impulse suppressor configured for attenuating the impulse in response to the presence of the impulse as detected by the sound impulse detector.

12. The hearing device according to claim 8, further comprising a sound impulse suppressor configured for attenuating the impulse in response to the presence of the impulse as detected by the sound impulse detector;
    wherein the sound impulse suppressor is configured for attenuating the impulse with an amount that is a function of the sound environment class determined by the sound environment detector.

13. The hearing device according to claim 11, wherein the sound impulse suppressor is configured for attenuating the impulse in such a way that the receiver does not emit sound originating from the impulse.

14. The hearing device according to claim 11, wherein a signal processing parameter of the sound impulse suppressor is adjustable in accordance with a user input.

15. The hearing device according to claim 1, wherein the hearing device is a hearing aid, and wherein the signal processor comprises a hearing loss processor that is configured to process the audio signal in accordance with a predetermined signal processing algorithm to generate a hearing loss compensated audio signal compensating a hearing loss of the user.

16. The hearing device according to claim 15, wherein the hearing loss processor comprises a dynamic range compressor.

17. The hearing device according to claim 1, wherein the hearing device is a hearing protector comprising a passive dampener configured for dampening sound, and wherein at least a part of the passive dampener is configured for occluding a part of an ear canal of the user.

18. A method comprising:
    converting sound into an audio signal;
    subjecting the audio signal to a frequency transformation to obtain a frequency transformed audio signal;
    detecting a presence of an impulse in the audio signal based on the frequency transformed audio signal;
    processing the audio signal into a processed audio signal in response to the detected presence of the impulse in the audio signal;
    converting the processed signal into an output sound signal; and
    emitting the output sound signal towards an eardrum of a human.

* * * * *